(12) United States Patent
Yamada et al.

(10) Patent No.: US 8,318,326 B2
(45) Date of Patent: *Nov. 27, 2012

(54) FUSED POLYCYCLIC COMPOUNDS AND ORGANIC LIGHT-EMITTING DEVICE USING THE SAME

(75) Inventors: Naoki Yamada, Inagi (JP); Minako Nakasu, Tokyo (JP); Satoshi Igawa, Fujisawa (JP); Masashi Hashimoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/078,806

(22) Filed: Apr. 1, 2011

(65) Prior Publication Data

US 2011/0175077 A1 Jul. 21, 2011

Related U.S. Application Data (63) Continuation of application No. 12/275,964, filed on Nov. 21, 2008, now Pat. No. 7,939,185.

(30) Foreign Application Priority Data

Nov. 27, 2007 (JP) ................................ 2007-306108

(51) Int. Cl.
*H01L 51/54* (2006.01)
(52) U.S. Cl. .................. 428/690; 257/40; 257/E51.028; 313/504; 585/27
(58) Field of Classification Search .................. None
See application file for complete search history.

(56) References Cited

U.S. PATENT DOCUMENTS

| | | | |
|---|---|---|---|
| 2003/0235713 A1* | 12/2003 | Suzuki et al. | 428/690 |
| 2007/0007538 A1* | 1/2007 | Ono et al. | 257/79 |
| 2011/0175077 A1* | 7/2011 | Yamada et al. | 257/40 |

* cited by examiner

*Primary Examiner* — Jennifer Chriss
*Assistant Examiner* — J. L. Yang
(74) *Attorney, Agent, or Firm* — Canon U.S.A., Inc., IP Division (57) ABSTRACT

A fused polycyclic compounds is represented by the general formula (I):

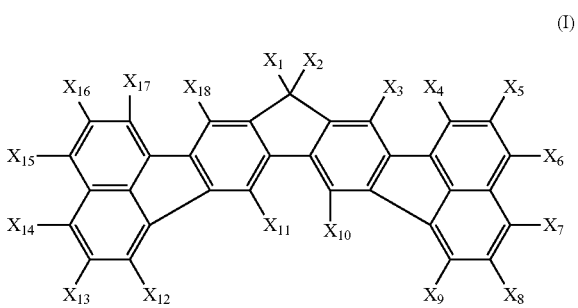

(I)

wherein $X_1$ to $X_{18}$ each represent, independently of one another, a hydrogen atom, a halogen atom, a cyano group, a nitro group, a substituted or unsubstituted alkyl group, a substituted or unsubstituted alkoxy group, a substituted or unsubstituted alkenyl group, a substituted or unsubstituted alkynyl group, a substituted or unsubstituted aralkyl group, a substituted amino group, a substituted or unsubstituted aryl group, or a substituted or unsubstituted heterocyclic group.

13 Claims, 3 Drawing Sheets

FUSED POLYCYCLIC COMPOUNDS AND ORGANIC LIGHT-EMITTING DEVICE USING THE SAME

CROSS REFERENCE TO RELATED APPLICATIONS

This application is a Continuation of U.S. patent application Ser. No. 12/275,964 filed Nov. 21, 2008, which claims priority to Japanese Patent Application No. 2007-306108 filed Nov. 27, 2007, each of which are hereby incorporated by reference in their entireties.

BACKGROUND OF THE INVENTION

1. Field of the Invention

The present invention generally relates to a fused polycyclic compound and an organic light-emitting device using the compound.

2. Description of the Related Art

An organic light-emitting device is a device having an anode, a cathode, and a thin film that contains a fluorescent or phosphorescent organic compound and is interposed between the anode and the cathode. Holes (positive holes) and electrons are injected from the respective electrodes, whereby excitons of the fluorescent or phosphorescent compound are produced. When the excitons return to a ground state, the organic light-emitting device emits light.

Recent progress in the development of the organic light-emitting device has been remarkable, and the properties of the device can enable a thin and light weight light-emitting device with a high luminance at a low applied voltage, a variety of emission wavelengths, and a high-speed response. This suggests that the devices have the potential to find use in a wide variety of applications.

However, an optical output with a higher luminance or a higher conversion efficiency is still presently being sought. In addition, there remains a need for organic light-emitting devices having improved durability, such as those having a reduced change over time due to long-term use and reduced degradation due to an atmospheric gas containing oxygen, moisture or the like.

Furthermore, when the device is used for a full-color display or the like, the device may need to be capable of emission of blue, green, or red light with good color purity.

It has been proposed to use a fused polycyclic compound such as fluoranthene as a constituent material of the light-emitting device. A fluoranthene compound used as a constituent material of the light-emitting device and a light-emitting device using the fluoranthene compound have been disclosed in Japanese Patent Application Laid-Open No. H10-189248.

SUMMARY OF THE INVENTION

In one embodiment, a fused polycyclic compound in accordance with the present invention is represented by the following general formula (I):

(I)

wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, and $X_{18}$ each represent, independently of one another, a hydrogen atom, a halogen atom, a cyano group, a nitro group, a substituted or unsubstituted alkyl group, a substituted or unsubstituted alkoxy group, a substituted or unsubstituted alkenyl group, a substituted or unsubstituted alkynyl group, a substituted or unsubstituted aralkyl group, a substituted amino group, a substituted or unsubstituted aryl group, or a substituted or unsubstituted heterocyclic group.

Further features of the present invention will become apparent from the following description of exemplary embodiments with reference to the attached drawings.

DESCRIPTION OF THE EMBODIMENTS

First, an embodiment of a fused polycyclic compound in accordance with the present invention will be described. The fused polycyclic compound according to this embodiment of the present invention is represented by the following general formula (I).

(I)

In the general formula (I), $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, and $X_{18}$ each represent, independently of one another, a hydrogen atom, a halogen atom, a cyano group, a nitro group, a substituted or unsubstituted alkyl group, a substituted or unsubstituted alkoxy group, a substituted or unsubstituted alkenyl group, a substituted or unsubstituted alkynyl group, a substituted or unsubstituted aralkyl group, a substituted amino group, a substituted or unsubstituted aryl group, or a substituted or unsubstituted heterocyclic group. In one version, when the stability of the compound is taken into consideration, $X_1$ and $X_2$ may each represent a substituted or unsubstituted alkyl group. In another version, it may also be the case that at least one of $X_1$ to $X_{18}$ is a substituted or unsubstituted aryl group, or a substituted or unsubstituted heterocyclic group. The introduction of an aryl group or a heterocyclic group, which is a relatively large substituent, may also produce the effect of avoiding intermolecular overlapping in certain cases. Thereby, the sublimation property and evaporation stability of the compound itself may be improved, the crystallinity may be reduced and the glass transition temperature may be increased, whereby the stability of the compound when formed into a thin film can be improved. Furthermore, the substitution with an aryl group (e.g. a fused polycyclic group such as fluorenyl, pyrenyl, perylenyl, anthracenyl or naphthyl group) having a high fluorescence quantum yield may increase the effect of improving the fluorescence quantum yield.

Examples of halogen atoms represented by $X_1$ to $X_{18}$ include fluorine, chlorine, bromine, and iodine.

Examples of alkyl groups represented by $X_1$ to $X_{18}$ may include, but are not limited to, methyl, ethyl, normal propyl, isopropyl, normal butyl, tert-butyl, sec-butyl, octyl, 1-adamantyl, and 2-adamantyl groups.

Examples of alkoxy groups represented by $X_1$ to $X_{18}$ may include, but are not limited to, methoxy, ethoxy, and propoxy groups.

Examples of alkenyl groups represented by $X_1$ to $X_{18}$ may include, but are not limited to, vinyl, propenyl, butenyl, phenylvinyl, and diphenylvinyl groups.

Examples of alkynyl groups represented by $X_1$ to $X_{18}$ may include, but are not limited to, ethynyl, propynyl, butynyl, and phenethynyl groups.

Examples of aralkyl groups represented by $X_1$ to $X_{18}$ may include, but are not limited to, benzyl and phenethyl groups.

Examples of substituted amino groups represented by $X_1$ to $X_{18}$ may include, but are not limited to, dimethylamino, diethylamino, dibenzylamino, diphenylamino, ditolylamino, di-tert-butylamono, dianisolylamino, and naphthylphenylamino groups.

Examples of aryl groups represented by $X_1$ to $X_{18}$ may include, but are not limited to, phenyl, biphenyl, terphenyl, naphthyl, pentalenyl, indenyl, azulenyl, anthryl, pyrenyl, indacenyl, acenaphthenyl, phenanthryl, phenalenyl, fluoranthenyl, benzofluoranthenyl, acephenanthryl, aceanthryl, triphenylenyl, chrysenyl, naphthacenyl, perylenyl, pentacenyl, and fluorenyl groups.

Examples of heterocyclic groups represented by $X_1$ to $X_{18}$ may include, but are not limited to, thienyl, pyrrolyl, pyridyl, bipyridyl, oxazolyl, oxadiazolyl, thiazolyl, thiadiazolyl, terthienyl, quinolyl, imidazolyl, carbazolyl, acridinyl, and phenanthrolyl.

Examples of substituents which the above described alkyl groups, alkoxy groups, alkenyl groups, alkynyl groups, aralkyl groups, aryl groups and heterocyclic groups may further have may include, but are not limited to: alkyl groups such as methyl, ethyl, propyl, and tert-butyl groups; aralkyl groups such as benzyl and phenethyl groups; aryl groups such as phenyl, biphenyl, naphthyl, pyrenyl, anthryl, fluorenyl groups, and substituents derived from the following fused polycyclic rings:

heterocyclic groups such as thienyl, pyrrolyl, and pyridyl groups; amino groups such as dimethylamino, diethylamino, dibenzylamino, diphenylamino, ditolylamino, and dianisolylamino groups; alkoxy groups such as methoxy, ethoxy, and propoxy groups; aryloxy groups such as phenoxy group; halogen atoms such as fluorine and chlorine; a cyano group; and a nitro group.

The substituents represented by $X_1$ to $X_{18}$ may be the same or different.

Specific examples of the fused polycyclic compounds in accordance with the present invention are shown below. However, it should be understood that the examples shown herein are not intended to limit the present invention.

1-1

1-2

1-3

1-4

1-5

1-6

1-7

1-8

1-9

1-10

1-11

1-12

1-13

1-14

1-15

1-16

1-17

1-18

1-19

1-20

1-21

2-1

2-2

2-3

2-4

2-5

2-6

2-7

2-8

2-9

2-10

-continued

2-11

2-12

2-13

2-14

2-15

2-16

2-17

2-18

2-19

2-20

2-21

2-22

2-23

2-24

2-25

2-26

2-27

Next, embodiments of the organic light-emitting device in accordance with the present invention will be described in detail.

The organic light-emitting device is constituted of an anode and a cathode, and a layer including an organic compound and interposed between the anode and the cathode.

Hereinafter, embodiments of the organic light-emitting device in accordance with the present invention will be described in detail with reference to the drawings. First, reference numerals in the figures are described. In the figures, reference numeral 1 denotes a substrate; 2 an anode; 3 a light-emitting layer; 4 a cathode; 5 a hole-transporting layer; 6 an electron-transporting layer; 7 a hole injection layer; 8 a hole/exciton blocking layer; and 10, 20, 30, 40, and 50 each denote an organic light-emitting device.

Figure 1:
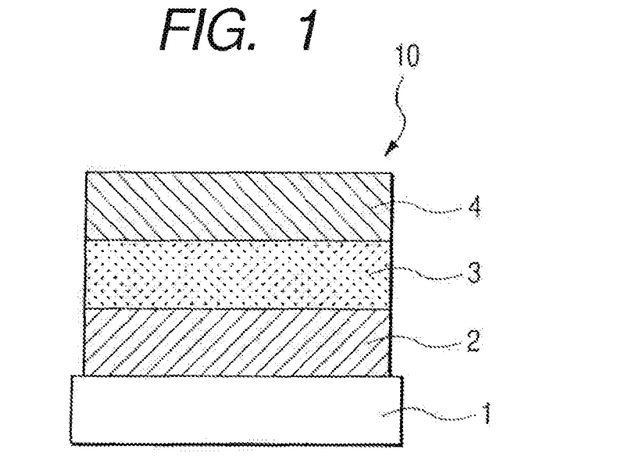
FIG. 1 is a cross-sectional view illustrating a first embodiment of an organic light-emitting device of the present invention.

FIG. 1 is a schematic cross-sectional view illustrating a first embodiment of an organic light-emitting device in accordance with the present invention. In the organic light-emitting device 10 shown in FIG. 1, there are sequentially provided on a substrate 1, an anode 2, a light-emitting layer 3 and a cathode 4. The configuration of the organic light-emitting device 10 shown in FIG. 1 may be useful, for example, when the light-emitting layer 3 comprises a compound having both hole transporting ability and electron transporting ability, as well as light emitting ability, or as another example when the light-emitting layer 3 comprises a mixture of compounds, the compounds each having at least one of the characteristics of hole transporting ability, electron transporting ability and light emitting ability.

Figure 2:
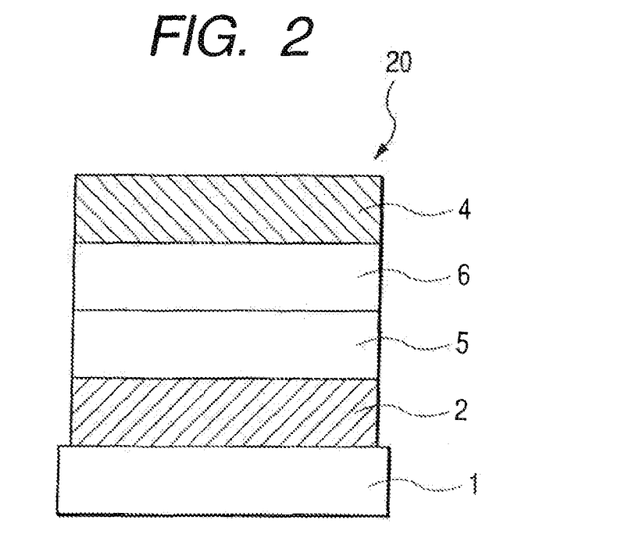
FIG. 2 is a cross-sectional view illustrating a second embodiment of the organic light-emitting device of the present invention.

FIG. 2 is a schematic cross-sectional view illustrating a second embodiment of an organic light-emitting device in accordance with the present invention. In the organic light-emitting device 20 shown in FIG. 2, there are sequentially provided on a substrate 1, an anode 2, a hole-transporting layer 5, an electron-transporting layer 6, and a cathode 4. The configuration of the organic light-emitting device 20 shown in FIG. 2 may be useful, for example, when a light-emitting organic compound having any one of hole transporting ability and electron transporting ability, and an organic compound having only hole-transporting ability or electron transporting ability, are used in combination with one another. Incidentally, in the organic light-emitting device 20, either of the hole-transporting layer 5 or the electron-transporting layer 6 may also serve as a light-emitting layer.

Figure 3:
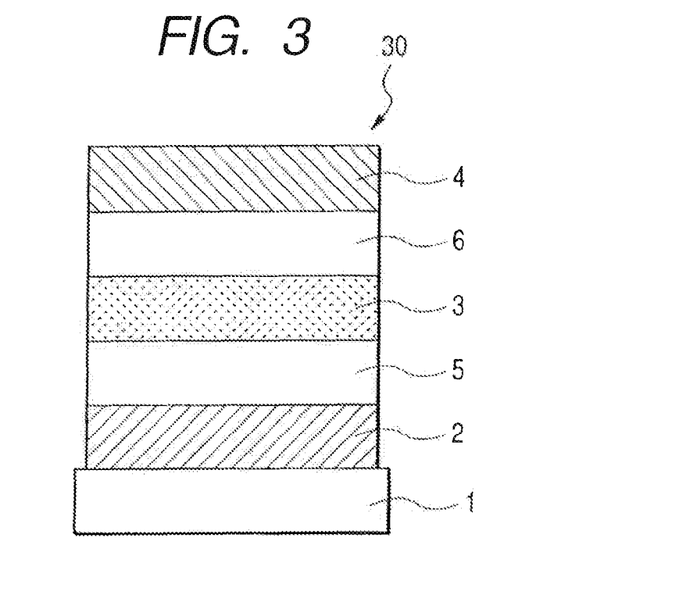
FIG. 3 is a cross-sectional view illustrating a third embodiment of the organic light-emitting device of the present invention.

FIG. 3 is a schematic cross-sectional view illustrating a third embodiment of an organic light-emitting device in accordance with the present invention. The embodiment of the organic light-emitting device 30 shown in FIG. 3 is different from the embodiment of the organic light-emitting device 20 shown in FIG. 2, in that a light-emitting layer 3 is additionally provided between a hole-transporting layer 5 and an electron-transporting layer 6. The embodiment of the organic light-emitting device 30 shown in FIG. 3 has a configuration in which the functions of carrier transportation and light emission are separated from each other, so that organic compounds having hole-transporting properties, electron-transporting properties and light-emitting properties, can be suitably combined and used. Therefore, since the degree of freedom in selecting materials can be significantly increased, and further since various compounds having different emission wavelengths can be used, a wide variety of emission hues can be provided. Further, it may also become possible to effectively confine carriers or excitons in the light-emitting layer 3, thereby improving the emission efficiency thereof.

Figure 4:
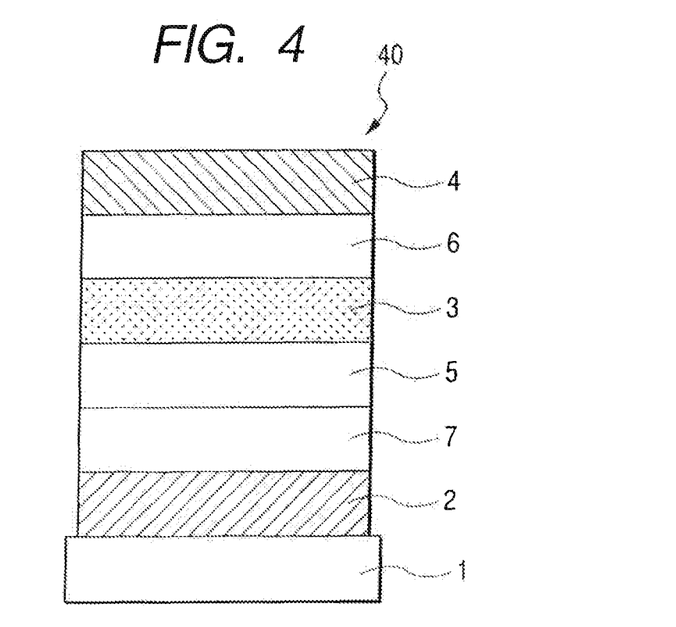
FIG. 4 is a cross-sectional view illustrating a fourth embodiment of the organic light-emitting device of the present invention.

FIG. 4 is a schematic cross-sectional view illustrating a fourth embodiment of an organic light-emitting device in accordance with the present invention. The embodiment of the organic light-emitting device 40 shown in FIG. 4 is different from the embodiment of the organic light-emitting device 30 shown in FIG. 3, in that a hole injection layer 7 is additionally provided between an anode 2 and a hole-transporting layer 5. In the embodiment of the organic light-emitting device 40 shown in FIG. 4, by additionally providing the hole injection layer 7, the adhesion between the anode 2 and the hole-transporting layer 5 or the hole injection property may be improved, so that the driving voltage can be effectively reduced.

Figure 5:
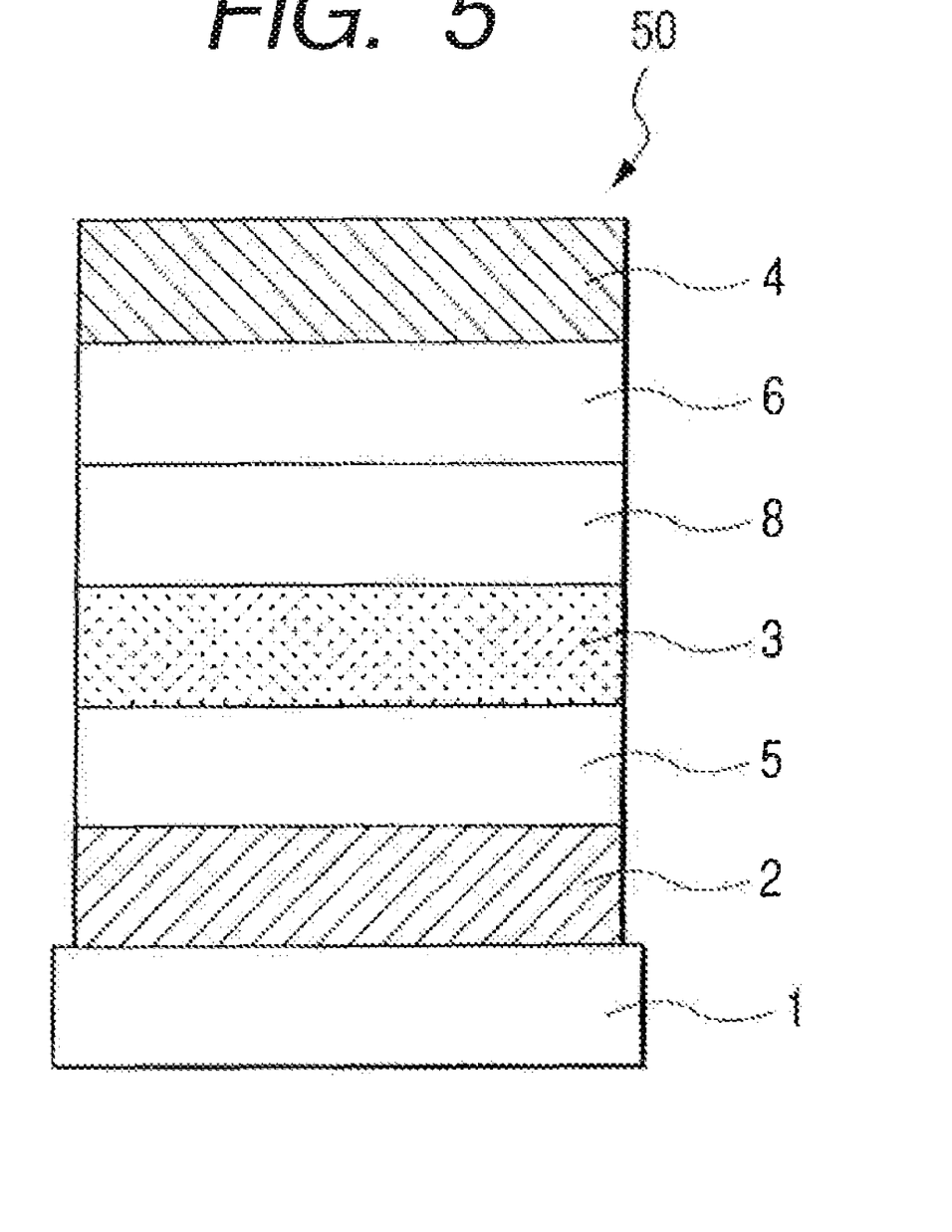
FIG. 5 is a cross-sectional view illustrating a fifth embodiment of the organic light-emitting device of the present invention.

FIG. 5 is a schematic cross-sectional view illustrating a fifth embodiment of an organic light-emitting device in accordance with the present invention. The organic light-emitting device 50 shown in FIG. 5 is different from the organic light-emitting device 30 shown in FIG. 3 in that a layer (hole/exciton blocking layer 8) for blocking holes or excitons from passing to a cathode 4 side is additionally provided between a light-emitting layer 3 and an electron-transporting layer 6. In the embodiment of the organic light-emitting device 50 shown in FIG. 5, by using a compound having a significantly high ionization potential as the constituent material of the hole/exciton blocking layer 8, electrons or excitons may be prevented from passing through the light-emitting layer 4 to the anode 2 side. Therefore, it the configuration may be effective for improving the emission efficiency of the device.

FIGS. 1 to 5 show examples of basic device configurations, and the configuration of the organic light-emitting device using the compound according to the present invention is not intended to be limited thereto. For example, it is possible to adopt various other layer structures, such as one in which an insulating layer is formed at an interface between an electrode and an organic layer, one in which an adhesive layer or an interference layer is formed, and one in which a hole-transporting layer is composed of two layers having different ionization potentials.

The fused polycyclic compound in accordance with the present invention can be used as a constituent material of an organic light-emitting device having any one of the configurations shown in FIGS. 1 to 5.

In the organic light-emitting device in accordance with the present invention, the layer including an organic compound comprises at least one of the fused polycyclic compounds of the present invention. Specifically, the term "layer including an organic compound" as employed herein may refer to any one of the light-emitting layer 3, hole-transporting layer 5, electron-transporting layer 6, hole injection layer 7, and hole/exciton blocking layer 8, as shown for example in FIGS. 1 to 5.

In one version, the fused polycyclic compound of the present invention is contained in at least one of the light-emitting layer 3, hole-transporting layer 5, and electron-transporting layer 6. This can provide an organic light-emitting device having high emission efficiency and long life. For example, the fused polycyclic compound of the present invention may be contained in the light-emitting layer 3.

In the case where the fused polycyclic compound in accordance with the present invention is used as a constituent material of the light-emitting layer 3 of the organic light-emitting device, in order to increase the emission efficiency of the organic light-emitting device, the fluorescence quantum yield of the light-emitting center material itself may be large.

According to one aspect, the fused polycyclic skeleton that forms a basic skeleton of the fused polycyclic compound in accordance with the present invention may have a highly rigid skeleton. Therefore, the use of the fused polycyclic compound of the present invention can improve the fluorescence quantum yield and emission efficiency of the device.

Furthermore, in order to provide a durable organic light-emitting device, an organic compound having chemical stability may be provided as the constituent material of the device.

According to another aspect, the fused polycyclic compound in accordance with the present invention, because of the electron-withdrawing effect of the 5-membered ring structures contained in the basic skeleton, has a reduced reactivity in terms of an electrophilic reaction of singlet oxygen molecules or the like. Therefore, embodiments of the fused polycyclic compound in accordance with the present invention may be chemically stable. According to a further aspect, embodiments of the fused polycyclic compound in accordance with the present invention contain three 5-membered ring structures in the basic skeletons. Thus, embodiments of the fused polycyclic compound in accordance with the present invention may be higher in chemical stability than fluoranthene, benzofluoranthene or the like, which have a basic skeleton with only one 5-membered ring structure.

In yet another aspect, embodiments of the fused polycyclic compound in accordance with the present invention may have electron injection properties because of the electron-withdrawing property of the 5-membered ring structures contained in the basic skeleton. Therefore, the use of the fused polycyclic compound of the present invention as a constituent material of an organic light-emitting device may enable the driving voltage of the device to be reduced. Moreover, because the fused polycyclic compound in accordance with the present invention contains three 5-membered ring structures in the basic skeleton, the effect of reducing the driving voltage of the device may be higher than fluoranthene, benzofluoranthene or the like, which have a basic skeleton with only one 5-membered ring structure.

Furthermore, in embodiments of the fused polycyclic compound in accordance with the present invention, by introduction of appropriate substituents, the HOMO and LUMO levels can be easily adjusted. This may enable molecular design of a material while taking into consideration the balance of injections of carriers such as holes and electrons. Further, the introduction of appropriate substituents may also enable molecular design of light-emitting materials corresponding to various emission colors.

In the case where the fused polycyclic compound in accordance with the present invention is used as a constituent material of the light-emitting layer 3, the compound can be used in various embodiments, and a long-life device having good color purity and high emission efficiency can be obtained. Examples of such embodiments may include: an embodiment where the light-emitting layer 3 comprises the fused polycyclic compound of the present invention alone; and an embodiment where the light-emitting layer 3 comprises both a guest and a host. In the both embodiments, a long-life device having good color purity and high emission efficiency can be obtained.

In the case where the fused polycyclic compound in accordance with the present invention is used as a guest for the light-emitting layer 3, in order to provide an organic light-emitting device having a stable amorphous film, the corresponding host can be, but is not limited to, a derivative of a fused polycyclic compound. Meanwhile, in order to provide a highly efficient and durable organic light-emitting device, the host itself may have high fluorescence quantum yield and chemical stability. Therefore, in one embodiment, the derivative of a fused polycyclic compound used as a host for the light-emitting layer 3 may be at least one of a fluorene derivative, a pyrene derivative, a fluoranthene derivative, a benzofluoranthene derivative, and the like. These fused polycyclic compound derivatives may have high fluorescence quantum yield and chemical stability.

In the case where the fused polycyclic compound in accordance with the present invention is used as a guest for the light-emitting layer 3, the content, based on the total weight of the materials constituting the light-emitting layer 3, may be 0.1% by weight or more and 30% by weight or less. In one version, the content is selected to inhibit concentration quenching, such as a content of 0.1% by weight or more and 15% by weight or less.

In the case where the fused polycyclic compound in accordance with the present invention is used as a host for the light-emitting layer 3, the corresponding guest (dopant) is not limited to any specific ones, and can be appropriately selected while for example taking into consideration factors such as the emission color or the like. Further, besides guests, at least one of a hole-transporting compound, an electron-transporting compound, and the like can also be used as a dopant. Examples of the hole-transporting compounds and electron-transporting compounds that can be used in the light-emitting layer 3 will be described later.

As described above, in the organic light-emitting device in accordance with the present invention, the fused polycyclic compound may be used as a constituent material of the light-emitting layer 3. Furthermore, in addition to the fused polycyclic compound, any known low-molecular-weight compounds or polymer compounds having at least one of hole-transporting property, light-emitting property, and electron-transporting property, can also be used as a constituent material of the light-emitting layer 3.

Examples of such hole-transporting compounds may include, but are not limited to: triarylamine derivatives, aryldiamine derivatives, phthalocyanine derivatives, porphyrin derivatives, poly(vinylcarbazole), poly(silylene), poly(thiophene) and other conductive polymers.

Examples of such light-emitting compounds may include, but are not limited to (besides the fused polycyclic compound in accordance with the present invention): triarylamine derivatives, fused ring aromatic compounds (e.g., naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, and rubrene), quinacridone derivatives, acridone derivatives, coumarine derivatives, pyran derivatives, nile red, pyrazine derivatives, benzoimidazole derivatives, benzothiazole derivatives, benzoxazole derivatives, stilbene derivatives, organometallic complexes (e.g., organoaluminum complexes such as tris(8-quinolinolato)aluminum, and organoberyllium complex), and polymer derivatives such as poly(phenylenevinylene) derivatives, poly(fluorene) derivatives, poly(phenylene) derivatives, poly(thienylenevinylene) derivatives and poly(acetylene) derivatives.

Examples of such electron-transporting compounds may include, but are not limited to: fused ring aromatic compounds (e.g. naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives and rubrene), oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organometallic complexes.

Examples of materials for the anode may include, but are not limited to, elemental metals such as lithium, sodium, potassium, calcium, magnesium, aluminum, indium, ruthenium, titanium, manganese, yttrium, silver, lead, tin, and chromium. Two or more of these metals may also be combined with each other to form alloys. For example, alloys such as lithium-indium, sodium-potassium, magnesium-silver, aluminum-lithium, aluminum-magnesium, and magnesium-indium can be used. Further, metal oxides such as indium tin oxide (ITO) can also be used. Of these electrode materials, one kind of material alone, or two or more kinds of materials together, may be used. Moreover, the anode may be of either a single-layer configuration or a multi-layer configuration.

Concrete examples of materials which can be used for the cathode may include, but are not limited to: elemental metals such as gold, platinum, silver, copper, nickel, palladium, cobalt, selenium, vanadium, and tungsten or alloys formed by combining two or more of them; and metal oxides such as tin oxide, zinc oxide, indium oxide, indium tin oxide (ITO), and indium zinc oxide. Further, conductive polymers such as polyaniline, polypyrrole, polythiophene, and poly(phenylene sulfide) can also be used. Of these electrode materials, one kind of material alone, or two or more kinds of materials together, may be used. The cathode may be of either a single-layer configuration or a multi-layer configuration.

Examples of the substrate used in the organic light-emitting device of the present invention may include, but are not limited to, an opaque substrate such as a metal substrate and a ceramic substrate; and a transparent substrate such as glass, quartz and plastic sheets.

In one embodiment, at least one of a color filter film, a fluorescent color conversion filter film, or a dielectric reflection film, can be used for a substrate to thereby control the emission color. Moreover, in the organic light-emitting device of the present invention, it may also be possible to provide a thin film transistor (TFT) on the substrate and form a device by connecting thereto.

In addition, as to the direction in which light is emitted from the device, any one of a bottom emission configuration (configuration in which light is emitted from a substrate side) and a top emission configuration (configuration in which light is emitted from a side opposite to the substrate side) may be adopted.

In one embodiment, a layer formed of an organic compound that comprises the fused polycyclic compound in accordance with the present invention may be formed by at least one of a vacuum evaporation process, a solution coating process, a transfer process using a laser, a spraying process, and the like. In particular, a layer formed by a vacuum evaporation or solution coating process may be less susceptible to crystallization and excellent in long-term stability. Layers that do not include the fused polycyclic compound in accordance with the present invention may also be formed by a process appropriately selected from at least one of a vacuum evaporation process, a solution coating process and the like.

EXAMPLES

The present invention will be described in more detail with reference to the examples. It is understood that these examples are not intended to limit the present invention thereto.

Example 1

Synthesis of Exemplified Compound 1-2

(a) Synthesis of Intermediate Compound 3-3
The following reagents and solvents were place in a 200 ml three-necked flask.
Compound 3-1: 0.600 g (1.00 mmol)
Compound 3-2: 0.905 g (2.5 mmol)
Toluene: 50 ml
Ethanol: 20 ml
To the reaction solution, an aqueous solution prepared by mixing 7 g of sodium carbonate and 50 ml of water was added dropwise with stirring in a nitrogen atmosphere at room temperature, followed by addition of 0.180 g of tetrakis (triphenylphosphine) palladium (0). The reaction solution was then heated to 77° C. and stirred for additional 5 hours. After completion of the reaction, the organic layer was extracted with toluene and dried over anhydrous sodium sulfate. Then the organic layer was filtered and the resultant filtrate was concentrated under reduced pressure to give a crude product. The crude product was then purified by silica gel column chromatography (developing solvent: toluene-heptane mixed solvent) to give 0.725 g of Intermediate Compound 3-3 as white crystal (yield 88%).

(b) Synthesis of Exemplified Compound 1-2

The following reagents and solvents were place in a 200 ml three-necked flask.

Compound 3-3: 0.700 g (0.844 mmol)
Lithium chloride: 0.179 g (4.22 mmol)
1,8-Diazabicyclo[5.4.0]-7-undecene: 0.321 g (2.11 mmol)
Dimethylformamide: 50 ml To the reaction solution, 0.118 g of bis(triphenylphosphine)palladium dichloride was added with stirring in a nitrogen atmosphere at room temperature. The reaction solution was then heated to 150° C. and stirred for additional 5 hours.

tography (developing solvent: toluene-heptane mixed solvent) to give 0.503 g of Exemplified Compound 1-2 as a light yellow crystal (yield 89%).

Then, 666 as M⁺ of Exemplified Compound 1-2 was confirmed by mass spectrometry.

Further, the structure of Exemplified Compound 1-2 was confirmed by $^1$H-NMR measurement.

$^1$H-NMR (CDCl$_3$, 400 MHz) σ (ppm): 8.40 (s, 2H), 8.11 (s, 2H), 8.026 (s, 2H), 8.00 (s, 2H), 7.79 (s, 2H), 7.78 (s, 2H), 1.72 (s, 6H), 1.54 (s, 36H)

The emission spectrum of Exemplified Compound 1-2 in $10^{-6}$ mol/l dilute toluene solution was measured using a fluorescence spectrophotometer (F-4500 (trade name); manufactured by Hitachi, Ltd.). Incidentally, the excitation wavelength was 340 nm. The measurement showed green emission spectrum having a maximum emission wavelength of 491 nm.

Example 2

Synthesis of Exemplified Compound 2-1

Exemplified Compound 2-1

After completion of the reaction, the reaction solution was cooled, 100 ml of water was added, followed by stirring for additional 30 minutes. The organic layer was extracted with toluene and dried over anhydrous sodium sulfate. Then the organic layer was filtered and the resultant filtrate was concentrated under reduced pressure to give a crude product. The crude product was then purified by silica gel column chroma- (a) Synthesis of Intermediate Compound 3-5

The following reagents and solvents were place in a 200 ml three-necked flask.

Compound 3-1: 0.670 g (1.12 mmol)
Compound 3-4: 1.19 g (2.68 mmol)
Toluene: 50 ml
Ethanol: 20 ml To the reaction solution, an aqueous solution prepared by mixing 7 g of sodium carbonate and 50 ml of water was added dropwise with stirring in a nitrogen atmosphere at room temperature, followed by addition of 0.180 g of tetrakis(triphenylphosphine)palladium(0). The reaction solution was then heated to 77° C. and stirred for additional 5 hours. After completion of the reaction, the organic layer was extracted with toluene and dried over anhydrous sodium sulfate. Then the organic layer was filtered and the resultant filtrate was concentrated under reduced pressure to give a crude product. The crude product was then purified by silica gel column chromatography (developing solvent: toluene-heptane mixed solvent) to give 0.838 g of Intermediate Compound 3-5 as a white crystal (yield 76%).

(b) Synthesis of Exemplified Compound 2-1

The following reagents and solvents were place in a 200 ml three-necked flask.

Compound 3-5: 0.800 g (0.810 mmol)
Lithium chloride: 0.171 g (4.05 mmol)
1,8-Diazabicyclo[5.4.0]-7-undecene: 0.308 g (2.03 mmol)
Dimethylformamide: 50 ml To the reaction solution, 0.114 g of bis(triphenylphosphine)palladium dichloride was added with stirring in a nitrogen atmosphere at room temperature. The reaction solution was then heated to 150° C. and stirred for additional 5 hours. After completion of the reaction, the reaction solution was cooled, 100 ml of water was added, followed by stirring for additional 30 minutes. The organic layer was extracted with toluene and dried over anhydrous sodium sulfate. Then the organic layer was filtered and the resultant filtrate was concentrated under reduced pressure to give a crude product. The crude product was then purified by silica gel column chromatography (developing solvent: toluene-heptane mixed solvent) to give 0.499 g of Exemplified Compound 2-1 as a light yellow crystal (yield 75%).

Then, 827 as M+ of Exemplified Compound 2-1 was confirmed by mass spectrometry.

Further, the structure of Exemplified Compound 2-1 was confirmed by $^1$H-NMR measurement.

$^1$H-NMR (CDCl$_3$, 400 MHz) σ (ppm): 8.38 (s, 2H), 8.07-8.00 (m, 8H), 7.84 (d, 2H), 7.81 (d, 2H), 7.73-7.66 (m, 6H) 7.61 (d, 2H), 7.48 (d, 2H), 7.41-7.34 (m, 4H), 1.75 (s, 6H), 1.60 (s, 12H)

The emission spectrum of Exemplified Compound 2-1 in $10^{-6}$ mol/l dilute toluene solution was measured in the same manner as in Example 1. Incidentally, the excitation wavelength was 340 nm. The measurement showed green emission spectrum having a maximum emission wavelength of 484 nm.

Example 3

An organic light-emitting device of the configuration shown in FIG. 3 was produced by the method shown below.

A film of indium tin oxide (ITO) was formed on a glass substrate (substrate 1) by sputtering to provide an anode 2. The film thickness of the anode 2 was 120 nm. Then, the substrate having the ITO film formed thereon was ultrasonically cleaned sequentially with acetone and isopropyl alcohol (IPA) and then washed with boiled IPA, followed by drying. The substrate was further cleaned with UV/ozone. The substrate treated as above was used as a transparent conductive support substrate.

Then, a 0.1% by weight solution of Exemplified Compound 4-1 represented by the following formula in chloroform was dropped and spin coated on the anode 2 to form a hole-transporting layer 5. The film thickness of the hole-transporting layer 5 was 11 nm.

Compound 4-1

Then, the transparent conductive support substrate having the hole-transporting layer 5 formed thereon was transferred to a vacuum chamber having an inner pressure of $10^{-5}$ Pa and subjected to vacuum evaporation by resistive heating to successively form an organic layer and an electrode layer, which are described below, whereby the organic light-emitting device was produced.

Specifically, Exemplified Compound 2-1 as a guest and Compound 4-2 of the formula below as a host were co-evaporated so that the weight concentration ratio was 2:95, to form a light-emitting layer 3. The film thickness of the light-emitting layer 3 was 30 nm. Then, Compound 4-3 of the formula below was evaporated to form an electron-transporting layer 6. The film thickness of the electron-transporting layer was 40 nm. Then, LiF was evaporated to form a first metal electrode layer. The film thickness of the first metal electrode layer was 0.5 nm. Further, Al was evaporated to form a second metal electrode layer. The film thickness of the second metal electrode layer was 150 nm. The first and second electrode layers function as a cathode 4. The organic light-emitting device was thus obtained.

Compound 4-2

-continued

Compound 4-3

When a voltage of 6.1 V was applied to the thus obtained device, a current flowed in the device. At this time, the current density was 88 mA/cm² and green light emission with an emission luminance of 11200 cd/m² was observed.

Further, when a voltage was continuously applied for additional 100 hours in a nitrogen atmosphere while keeping the current density at 165 mA/cm², it was confirmed that the rate of luminance degradation after the passage of 100 hours with respect to the initial luminance was small.

The above-mentioned examples are capable of providing an organic light-emitting device having an optical output with a high efficiency and a high luminance, and a high durability. Also, the fused polycyclic compounds of the above examples may exhibit excellent light-emitting characteristics as a part of a light-emitting device, and may have high stability.

While the present invention has been described with reference to exemplary embodiments, it is to be understood that the invention is not limited to the exemplary embodiments disclosed herein. The scope of the following claims is to be accorded the broadest interpretation so as to encompass all such modifications and equivalent structures and functions.

What is claimed is:

1. A full-color display, comprising an organic light-emitting device on a substrate, the organic light-emitting device comprising:
   an anode and a cathode; and
   a layer comprising an organic compound interposed between the anode and the cathode,
   wherein the layer comprising an organic compound contains at least one of the fused polycyclic compounds represented by the general formula (I):

(I)

wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, and $X_{18}$ each represent, independently of one another, a hydrogen atom, a halogen atom, a cyano group, a nitro group, a substituted or unsubstituted alkyl group, a substituted or unsubstituted alkoxy group, a substituted or unsubstituted alkenyl group, a substituted or unsubstituted alkynyl group, a substituted or unsubstituted aralkyl group, a substituted amino group, a substituted or unsubstituted aryl group, or a substituted or unsubstituted heterocyclic group.

2. The full-color display according to claim 1, wherein $X_1$ and $X_2$ each represent a substituted or unsubstituted alkyl group.

3. The full-color display according to claim 1, wherein the layer comprising the organic compound is a light-emitting layer, and the organic light-emitting device comprises, in addition to the layer comprising the organic compound, another layer comprising the organic compound disposed between the anode and the cathode.

4. The full-color display according to claim 1, wherein the substrate is opaque.

5. The full-color display according to claim 1, wherein the substrate is transparent.

6. The full-color display according to claim 1, comprising a color filter film.

7. The full-color display according to claim 1, comprising a fluorescent color conversion filter film.

8. The full-color display according to claim 1, comprising a dielectric reflection film.

9. The full-color display according to claim 1, comprising a thin film transistor connected to the organic light-emitting device.

10. The full-color display according to claim 1, wherein light emitted by the organic light-emitting device exits outside through the substrate.

11. The full-color display according to claim 1, wherein light emitted by the organic light-emitting device exits outside from a side opposite to the substrate side.

12. The full-color display according to claim 1, wherein the layer is a light-emitting layer, the light-emitting layer comprises a host and a guest, and the guest is the organic compound.

13. The full-color display according to claim 12, wherein the organic light-emitting device emits green light.

\* \* \* \* \*